United States Patent [19]

Crawford et al.

[11] Patent Number: 5,707,363
[45] Date of Patent: Jan. 13, 1998

[54] GUIDEWIRE RETENTION DEVICE

[75] Inventors: Mark A. Crawford; Glade H. Howell; Kenneth C. Musgrave; Timothy J. Erskine, all of Sandy, Utah

[73] Assignee: Becton Dickinson and Company, Franklin Lakes, N.J.

[21] Appl. No.: 609,154

[22] Filed: Feb. 29, 1996

[51] Int. Cl.⁶ .................................................. A61M 5/178
[52] U.S. Cl. ............................................ 604/165; 604/177
[58] Field of Search ................................ 604/164, 165, 604/166, 177, 178

[56] References Cited

U.S. PATENT DOCUMENTS

| | | | |
|---|---|---|---|
| 4,846,804 | 7/1989 | Davis | 604/164 |
| 5,135,502 | 8/1992 | Koenig | 604/165 |
| 5,171,245 | 12/1992 | Cezana | 606/86 |
| 5,437,643 | 8/1995 | Transue | 604/164 |
| 5,437,645 | 8/1995 | Urban et al. | 604/165 |

*Primary Examiner*—Robert A. Hafer
*Assistant Examiner*—Luke Yeh
*Attorney, Agent, or Firm*—Eric M. Lee

[57] ABSTRACT

A guidewire retention device for use with a catheter or other medical device is disclosed herein. The guidewire retention device can be connected to a standard adapter at the proximal end of the catheter. It has an opening therein which can be placed in communication with the catheter lumen. This opening includes a large diameter portion and a small diameter portion and is preferably keyhole shaped. The large diameter portion allows a guidewire to easily pass therethrough while the small diameter portion does not. Thus, when a guidewire is located in the catheter lumen in the proper position, the guidewire can be fitted into the small diameter portion of the keyhole shaped opening to lock the guidewire with respect to the catheter. A raised icon on the guidewire retention device provides an indication to the clinician of how to use the guidewire retention device.

10 Claims, 3 Drawing Sheets

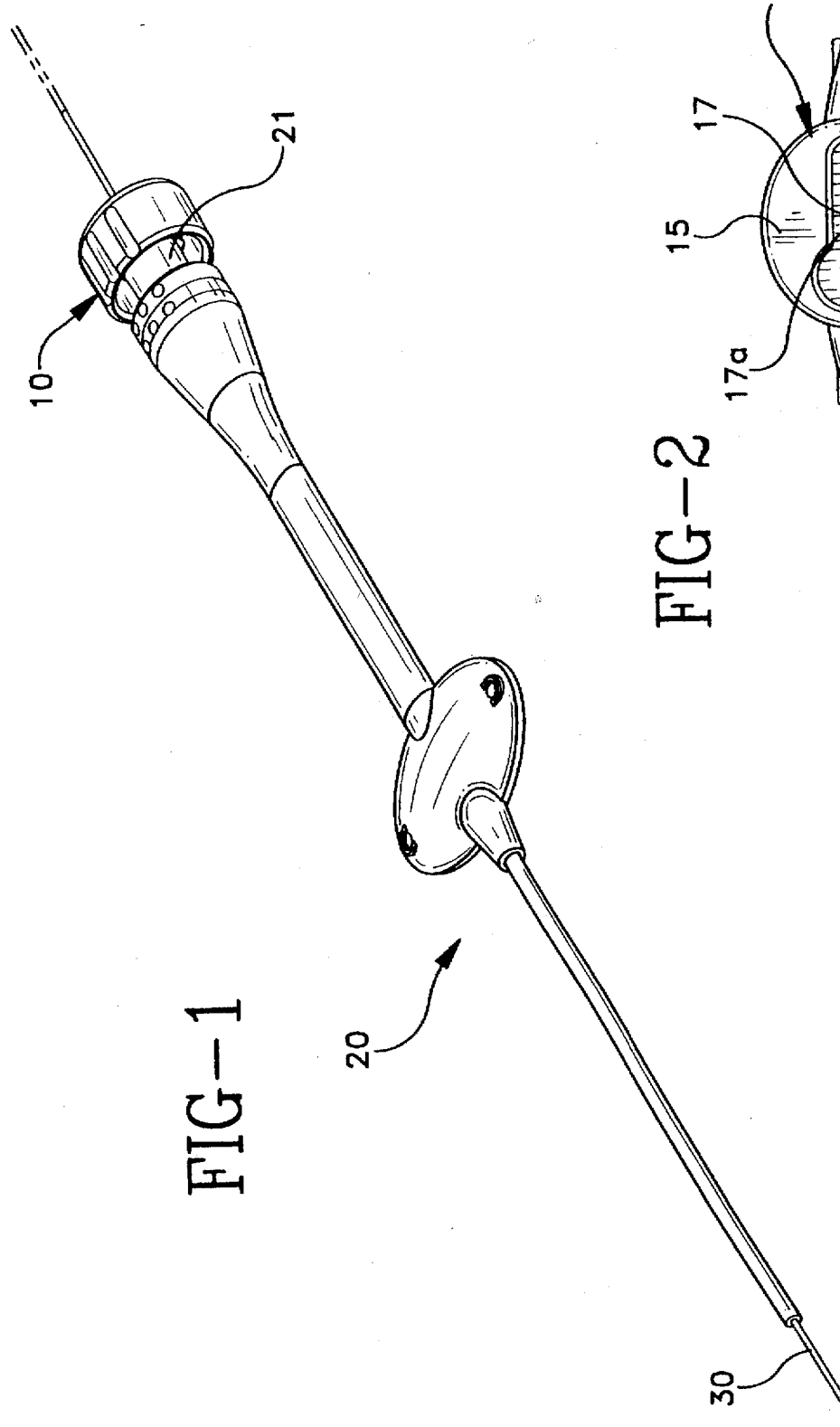

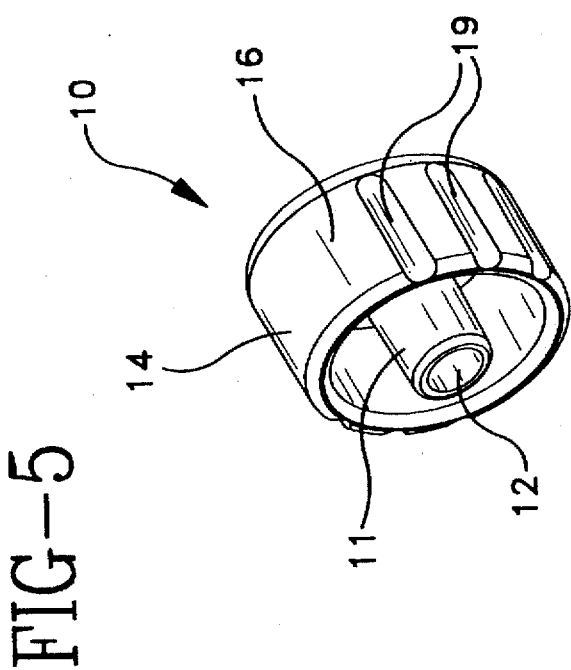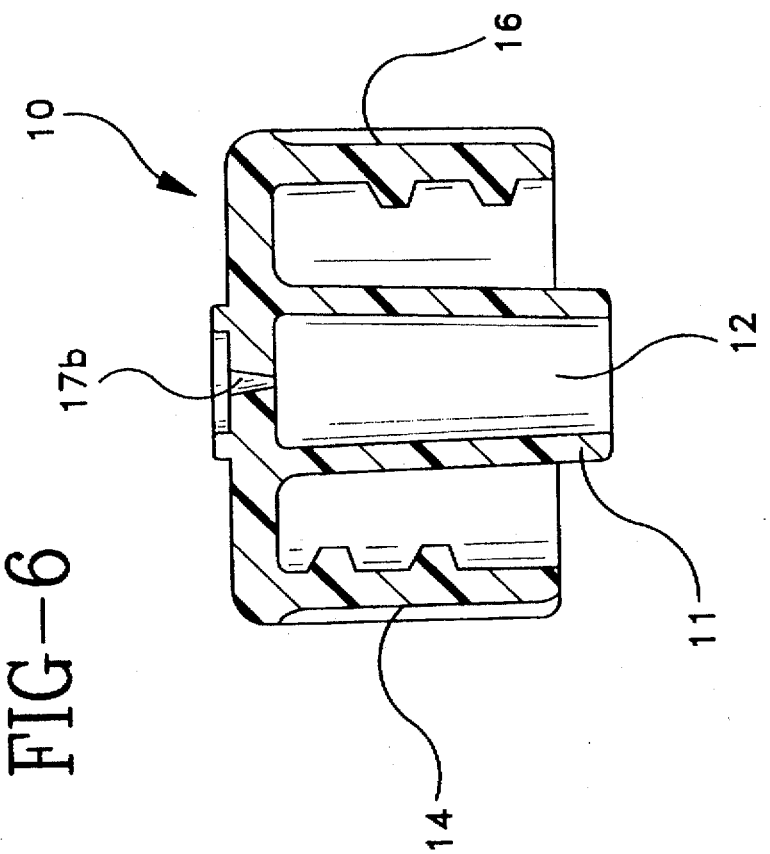

GUIDEWIRE RETENTION DEVICE

BACKGROUND OF THE INVENTION

This invention relates to a device that retains a guidewire in position with respect to a catheter. This invention has particular applicability to peripherally inserted central catheters (PICCs) but may also be useful with other catheters where guidewires are used to properly place the catheter in a patient's anatomy.

PICCs are typically used for IV therapy when the medicaments to be provided to the patient must be diluted quickly in the larger central veins of the patient, such as the auxiliary, subclavian or brachiocephalic vein or the superior vena cava, or could otherwise damage the smaller veins in the patient's hand or arm. In the past, central venous access catheters were used. Such catheters are placed directly into these larger veins by a physician. In contrast, PICCs are inserted peripherally into a vein in the patient's arm and maneuvered through the patient's venous system until the distal tip of the catheter is located in the superior vena cava.

In order to properly place a PICC into a patient, a guidewire may be used. These guidewires are generally made from some metal or alloy. Thus, they tend to be stiffer than a standard PICC which is made from a soft, flexible polymer such as silicone. When a guidewire is inserted into the catheter, the resulting structure is stiffer and thus more easily maneuvered through the patient's venous system so the distal tip of the catheter can be properly located.

It is important for the distal tip of the catheter and the distal tip of the guidewire to be substantially aligned. This ensures that the distal tip of the catheter remains relatively rigid for maneuverability and that the distal tip of the guidewire does not extend beyond the distal tip of the catheter to cause damage to the blood vessel or to adversely affect maneuverability. Unfortunately, current PICCs and guidewires do not have any simple mechanism to prevent unwanted relative axial movement between the guidewire and the catheter. Instead, the clinician typically bends the guidewire at the point that the guidewire exits the proximal end of the catheter by the luer adapter. This technique is insufficient because it does not positively maintain the relative axial position between the catheter and the guidewire. In addition, this technique damages the guidewire so that if there were any need to advance the guidewire through the catheter, the bend in the guidewire would make this difficult.

SUMMARY OF THE INVENTION

It is therefore an object of this invention to provide a mechanism for use with a catheter that maintains the relative axial position of the catheter and a guidewire.

It is another object of this invention to provide a mechanism for use with a catheter that maintains the relative axial position of the catheter and a guidewire without damaging the guidewire.

The guidewire retention device of this invention comprises a standard male luer adapter defining a lumen therein and having a proximal face with an opening comprising a large diameter portion and a small diameter portion, i.e. a keyhole shaped opening, therein. This keyhole shaped opening is in communication with the lumen that extends through the male luer adapter. The male luer adapter allows the guidewire retention device to be connected to a standard female luer adapter on the proximal end of the catheter so that the lumen in the male luer adapter is in communication with the catheter lumen. This allows a guidewire to extend through the catheter and the guidewire retention device. The keyhole shaped opening is provided with suitable dimensions such that the large diameter portion of the opening allows a guidewire to easily pass therethrough while the small diameter portion mechanically and frictionally engages the guidewire. Thus, when the guidewire retention device is connected to the female luer adapter on the proximal end of the catheter, a guidewire can extend through the catheter, the lumen of the male luer adapter of the guidewire retention device and the large diameter portion of the keyhole shaped opening. When the clinician aligns the distal ends of the catheter and the guidewire, the clinician can move the proximal portion of the guidewire into the small diameter portion of the keyhole shaped opening so the guidewire is locked in place relative to the catheter.

BRIEF DESCRIPTION OF THE DRAWINGS

The above and other objects and advantages of this invention will be apparent from the detailed description and drawings in which like parts are referred to by like numbers throughout, and in which:

FIG. 1 is a perspective view of a PICC and the guidewire retention device of this invention and a guidewire extending therethrough;

FIG. 2 is a rear elevation view of the guidewire retention device of this invention attached to the proximal end of the PICC as shown in FIG. 1;

FIG. 5 is a front perspective view of the guidewire retention device of this invention; and FIG. 6 is a cross-sectional view of the guidewire retention device of this invention taken along line 6—6 of FIG. 4.

DETAILED DESCRIPTION OF THE INVENTION

Figure 4:
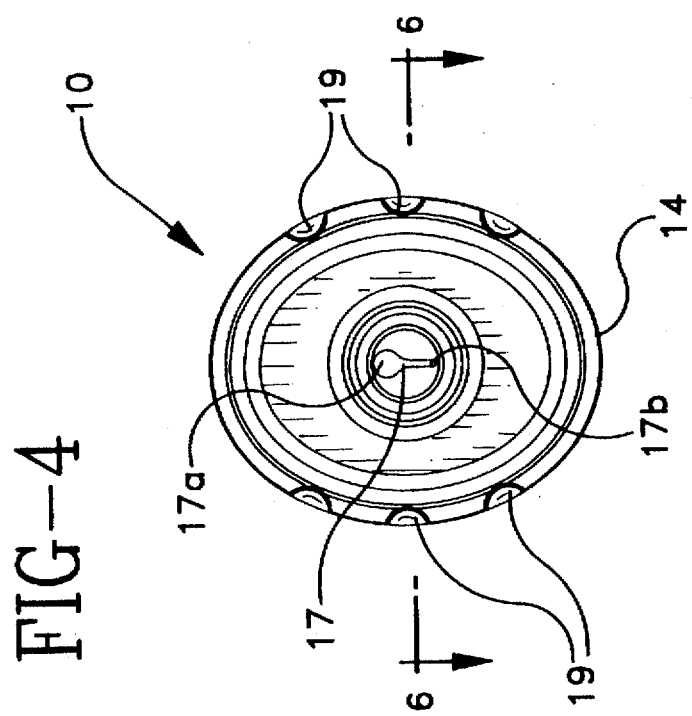
FIG. 4 is a front elevation view of the guidewire retention device of this invention.
Figure 3:
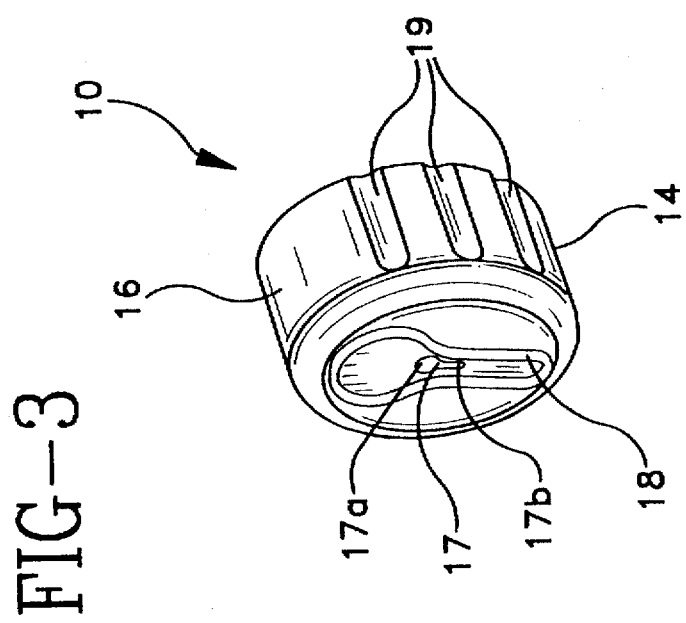
FIG. 3 is a rear perspective view of the guidewire retention device of this invention.

The guidewire retention device 10 of this invention is shown for use in connection with a PICC 20. However, it is to be understood that guidewire retention device 10 could be used with other catheters or medical devices where guidewire position relative to the catheter or medical device is important.

Guidewire retention device 10 includes a male luer adapter portion 11 and a cap portion 14. Guidewire retention device 10 may have a cross-section of any shape. However, guidewire retention device 10 preferably has an elliptical cross-section. Alternatively, guidewire retention device 10 could have a cross-section in the shape of an opening 17 formed therein. See discussion below concerning the configuration of opening 17. In addition, guidewire retention device 10 is formed from a relatively hard plastic such as polypropylene or polycarbonate.

Male luer adapter portion 11 defines an inner lumen 12 that extends therethrough. The outer surface of male luer portion 11 defines a luer slip configuration so that guidewire retention device 10 can be connected to the female luer adapter 21 of catheter 20. Alternatively, male luer adapter portion 11 could have a cylindrical configuration and the interior of cap portion 14 could be configured to include threads that engage the threads of female luer adapter 21. This alternative configuration would provide a greater mechanical connection between guidewire retention device 10 and catheter 20.

Cap portion 14 defines end face 15 and shroud 16. End face 15 defines opening 17 therein that is in communication with lumen 12. Opening 17 includes a large diameter portion 17a and a small diameter portion 17b. Opening 17 is preferably keyhole shaped. However, it is to be understood that opening 17 could have another configuration that includes a large diameter portion that allows a guidewire 30 to pass through and a small diameter portion that engages guidewire 30, see FIG. 1, to prevent movement therebetween. Preferably opening 17 is axially aligned with lumen 12.

Large diameter portion 17a should have a diameter slightly larger than the diameter of guidewire 30 that is to be used with catheter 20. Small diameter portion 17b should have a diameter less than the diameter of guidewire 30. This diameter should be between about 0.001 inches to about 0.010 inches smaller than the diameter of guidewire 30. Preferably, the diameter of small diameter portion 17b is about 0.006 inches less than the diameter of guidewire 30. Preferably the sidewalls of small diameter portion 17b define knife edges. See FIG. 6. These knife edges preferably define an included angle, i.e. an angle between the sidewalls of small diameter portion 17b, of about 13.4 degrees, although an angle of between about 6 degrees and about 20 degrees would work. By forming the sides of small diameter portion 17b into knife edges guidewire 30 can be more effectively locked in small diameter portion 17b.

When guidewire 30 is aligned with large diameter portion 17a, guidewire 30 can freely move therethrough so the clinician can easily move guidewire 30 axially relative to catheter 20. This facilitates alignment of the distal tip of guidewire 30 with the distal tip of catheter 20 when guidewire 30 extends through lumen 22 of catheter 20. Once guidewire 30 and catheter 20 are properly axially aligned, the clinician can move guidewire 30 into small diameter portion 17b. Because small diameter portion 17b has a smaller diameter than guidewire 30, the edges of small diameter portion 17b mechanically and frictionally engage guidewire 30 effectively to lock guidewire 30 with respect to catheter 20.

Endface 15 may also include a raised icon 18 formed thereon. This provides the clinician with an indication of how guidewire 30 should be moved in opening 17 to "lock" or "unlock" guidewire 30 from guidewire retention device 10. Since opening 17 is quite small, raised icon 18 facilitates easy use of guidewire retention device 10. Preferably raised icon 18 has a keyhole shape. However, raised icon 18 does not have to be keyhole shaped but could have another shape that indicates the direction that guidewire 30 must be moved in order to lock and unlock guidewire 30 from guidewire retention device 10. In addition, as discussed above, endface 15 could be formed into the shape of opening 17 to provide this indication. In this circumstance there would be no need for raised icon 18.

Shroud 16 should be long enough so that the clinician can easily grasp guidewire retention device 10. A plurality of grooves 19 may be formed in shroud 16 to facilitate grasping guidewire retention device 10 by the clinician.

Thus, it is seen that a guidewire retention device is provided that maintains the relative axial position of a catheter and a guidewire without damaging the guidewire.

We claim:

1. A guidewire retention device, comprising:

a face portion defining an opening therein that has a first portion with a first diameter and a second portion radially offset from the first portion and having a second diameter smaller than the first diameter wherein the second portion is defined by sidewalls having an included angle between the sidewalls of between about 6 degrees and about 20 degrees; and a means for connecting the face portion to a medical device.

2. The guidewire retention device of claim 1 wherein the face portion is formed in the shape of the opening.

3. The guidewire retention device of claim 1 further comprising a raised icon on the face portion surrounding the opening.

4. A guidewire retention device, comprising:

a tubular portion having a proximal end and a distal end and a lumen extending therethrough; and a cap portion affixed to the proximal end of the tubular portion, the cap portion defining an opening therein in communication with the lumen wherein the opening has a first portion with a first diameter and a second portion radially offset from the first portion and having a second diameter smaller than the first diameter wherein the second portion is defined by sidewalls having an included angle between the sidewalls of between about 6 degrees and about 20 degrees.

5. The guidewire retention device of claim 4 further comprising a raised icon on the cap portion.

6. The guidewire retention device of claim 5 wherein the opening and the raised icon are keyhole shaped.

7. A catheter and guidewire assembly, comprising:

a catheter having a lumen therein, a distal end and a proximal end and an adapter at the proximal end;

a guidewire extending through the lumen in the catheter and having a distal end and a proximal portion extending proximally of the adapter of the catheter; and a guidewire retention device connected to the adapter and defining an opening therein having a first portion with a first diameter and a second portion radially offset from the first portion and having a second diameter smaller than the first diameter and wherein the proximal portion of the guidewire extends through the opening wherein the second portion is defined by sidewalls having an included angle between the sidewalls of between about 6 degrees and about 20 degrees.

8. The catheter and guidewire assembly of claim 7 wherein the second portion has a diameter between about 0.001 to about 0.010 inches less than a diameter of the guidewire.

9. The catheter and guidewire assembly of claim 8 wherein the guidewire retention device includes a raised icon thereon.

10. The catheter and guidewire assembly of claim 9 wherein the opening and the raised icon are keyhole shaped.

* * * * *